United States Patent [19]
Lacoste et al.

[11] Patent Number: 5,266,565
[45] Date of Patent: Nov. 30, 1993

[54] VANADIUM COMPLEXES

[75] Inventors: Jean-Michel Lacoste, Sevres; Jacques Duhault, Croissy sur Seine; Denis Ravel, Igny, all of France

[73] Assignee: Adir et Compagnie, Courbevoie, France

[21] Appl. No.: 909,107

[22] Filed: Jul. 2, 1992

[30] Foreign Application Priority Data

Jul. 3, 1991 [FR] France ................. 91 08253

[51] Int. Cl.$^5$ ............... A61K 31/555; A61K 31/28; C07F 11/00
[52] U.S. Cl. .................................. 514/114; 546/6; 514/492; 514/89; 556/42
[58] Field of Search .......... 556/42; 514/114, 492

[56] References Cited

PUBLICATIONS

Nakajima, Chem. Letters 1986, 1483.
Farmer, Inorg. Chem 13, 587 (1974).
Kolawale, J.C.S. Dalton 1241 (1981).
Khuhawar, J. Chem Soc. Pak 13, 10 (1991).
Khuhawar, J. Chem Soc Pakistan 12, 324 (1990).

*Primary Examiner*—Mark L. Berch
*Attorney, Agent, or Firm*—Gordon W. Hueschen

[57] ABSTRACT

Compounds of formula (I):

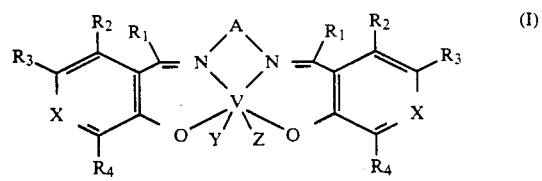

in which:

$R_1$ or $R_4$, which are identical or different, represent hydrogen or alkyl, $R_2$ represents hydrogenm or alkyl, hydroxymethyl, $-CH_2OPO(OH)_2$ or $-CH_2OPO(ONa)_2$, $R_3$ represents hydrogen, alkyl or hydroxyl or any one of the following groups:

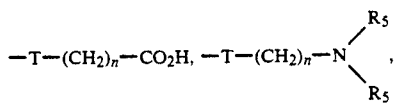

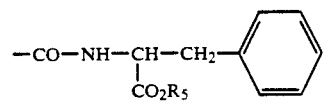

in which:

T represents oxygen or sulfur,
n represents an integer between 1 and 4,
$R_5$ represents hydrogen or alkyl,
X represents nitrogen, CH or $CR'_3$ (in which $R'_3$ has the same meaning as $R_3$ except in the case where $R_3$ represents hydroxyl),
A represents alkylene of formula $-(CH_2)_p$- in which p represents an integer between 2 and 4, optionally substituted by one or more linear or branched ($C_1-C_4$) alkyl, or any one of the following radicals:

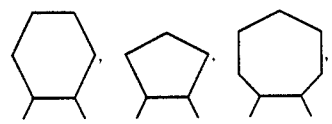

Y and Z together form oxygen or simultaneously represent two hydroxyl and in this case, the compound of formula (I) is positively charged, their isomers as well as their addition salts with a pharmaceutically acceptable acid or base.

10 Claims, No Drawings

VANADIUM COMPLEXES

The present invention relates to new vanadium complexes.

It has been found that orally-administered sodium vanadate possesses an antidiabetic efficacy (Science, 227, 1474, 1985). However, the diabetic state is characterized by a defect in the penetration of glucose into cells, which is due either to the absence of insulin (insulin-dependent diabetes), or to a reduced glucose tolerance or to a reduction in the efficacy of insulin at the peripheral tissue level (noninsulin-dependent diabetes), and which is linked to an increase in glycemia. The administration of insulin or insulin-like substances may correct these diabetic states. This is the case in particular for sodium vanadate as well as vanadium complexes described in Patents EP 305264 and JP 2-292217. These various complexes activate the transport of glucose and its metabolism. However, sodium vanadate exhibits a digestive intolerance which renders the absorption of the doses necessary for obtaining active blood concentrations difficult, in most cases.

The vanadium complexes described in the present invention possess, in addition to being new, the advantage of being better tolerated and less toxic, and they have demonstrated greater efficacy than the compounds described in the prior art, essentially due to a better bioavailability of the active biological entity.

The invention relates more particularly to new vanadium complexes of the formula (I):

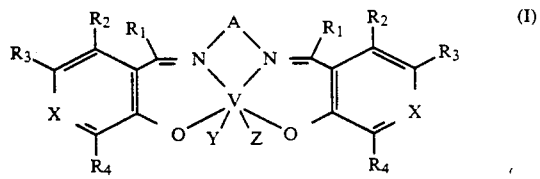

in which:

$R_1$ or $R_4$, which are identical or different, represent a hydrogen atom or a linear or branched $(C_1-C_6)$ alkyl group, $R_2$ represents a hydrogen atom, a linear or branched $(C_1-C_6)$ alkyl group, a hydroxymethyl group, a group $-CH_2OPO(OH)_2$ or a group $-CH_2OPO(ONa)_2$, $R_3$ represents a hydrogen atom, a linear or branched $(C_1-C_6)$ alkyl group, a hydroxyl group or any one of the following groups:

$$-T-(CH_2)_n-CO_2H$$

$$-T-(CH_2)_n-N\begin{matrix}R_5\\ \\R_5\end{matrix}$$

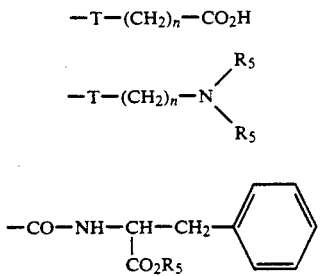

in which:

T represents an oxygen or sulfur atom,
n represents an integer between 1 and 4,
$R_5$ represents a hydrogen atom or a linear or branched $(C_1-C_6)$ alkyl group, X represents a nitrogen atom, a CH radical or a $CR'_3$ radical (in which $R'_3$ has the same meaning as $R_3$ except in the case where $R_3$ represents a hydroxyl group), A represents an alkylene radical of formula $-(CH_2)_p-$ in which p represents an integer between 2 and 4, optionally substituted by one or more linear or branched $(C_1-C_4)$ alkyl groups, or any one of the following radicals:

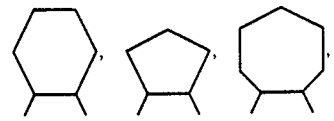

Y and Z together form an oxygen atom or, alternatively, simultaneously represent two hydroxyl groups, provided that:
a when:
A represents an ethylene group (optionally substituted by an alkyl group),
$R_2$, $R_3$ and $R_4$ simultaneously represent a hydrogen atom and $R_1$ represents a hydrogen atom or an alkyl group, then X does not represent a CH radical,
b when:
A represents a group

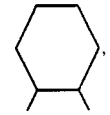

$R_1$, $R_2$ and $R_3$ simultaneously represent a hydrogen atom, and $R_4$ represents a hydrogen atom or an alkyl group, then X does not represent a CH radical, their isomers, enantiomers, diastereoisomers and epimers as well as their addition salts with a pharmaceutically acceptable acid or base.

Among the pharmaceutically acceptable acids, hydrochloric, hydrobromic, sulfuric, phosphonic, acetic, trifluoroacetic, lactic, pyruvic, malonic, succinic, glutaric, fumaric, tartaric, maleic, citric, ascorbic, oxalic, methanesulfonic and camphoric acids and the like, may be mentioned with no limitation being implied.

Among the pharmaceutically acceptable bases, sodium hydroxide, potassium hydroxide, triethylamine and tert-butylamine and the like, may be mentioned with no limitation being implied.

The invention also extends to the process for preparing compounds of formula (I), wherein two equivalents of a compound of formula (II):

$$\begin{matrix}R_2 & R^1\\R_3 & \\ & =O\\X & \\ & OH\\R_4\end{matrix} \quad (II)$$

in which $R_1$, $R_2$, $R_3$ and $R_4$ have the same meaning as in the formula (I), are reacted with one equivalent of a compound of formula (III), under an inert atmosphere:

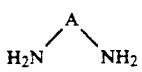

in which A has the same meaning as in the formula (I), to lead to the compound of formula (IV) whose isomers are optionally separated by a conventional separation technique, which compound:

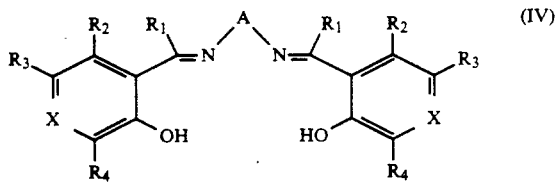

in which $R_1$, $R_2$, $R_3$, $R_4$, A and X have the same meaning as in the formula (I), is purified where appropriate by a conventional purification technique, and which compound is treated:
either with an aqueous solution of vanadyl sulfate pentahydrate in dichloromethane medium, or alternatively, after treating with sodium hydroxide, with an aqueous solution of vanadyl sulfate pentahydrate in tetrahydrofuran medium or alternatively with vanadyl sulfate in dimethylformamide medium,
to lead to the complex of formula (I/a), which is a specific example of the compounds of formula (I) in which the vanadium has the oxidation number IV:

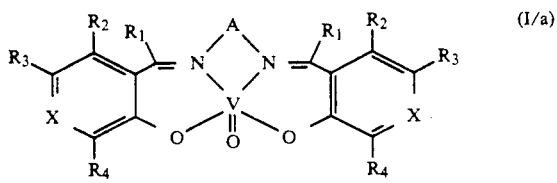

or with a solution of vanadyl sulfate in dimethylformamide in the presence of oxygen, according to the technique described by H. J. BIELIG et al., (Liebigs Ann. Chem., 580, 135, 1953)
to lead to the complex of formula (I/b), which is a specific example of the compounds of formula (I):

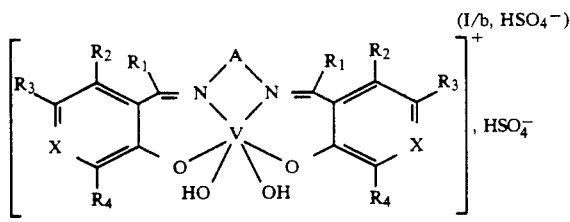

which compounds of formula (I/a) or (I/b) are purified, where appropriate, by a conventional purification technique and converted, if desired, to their addition salts with a pharmaceutically acceptable acid or base.

The compounds of the invention possess very useful pharmacological properties. They possess insulin-like activities not only in vitro but also in vivo. The results obtained both during the measurement of glucose metabolism and the capture of 2-deoxyglucose and during trials carried out on genetically insulin-resistant mice or on rats rendered diabetic by streptozotocin injection, show that the compounds of the invention can be used in the treatment of insulin-resistance states associated or unassociated with hyperglycemia and hyperinsulinemia such as type I and II diabetes, obesity and hypertension A favorable consequence of treatment using these compounds is the reduction in blood lipids which may contribute to the prevention of macroangiopathies.

The present invention also extends to the use of [N,N'-di(salicylidene)ethylenediamine]oxovanadium
(IV) (described by P. Pfeiffer et al., J. für Praktische Chemie, 149, 217, 1937) for producing pharmaceutical compositions which are useful in the treatment of diabetes.

The subject of the present invention is also the pharmaceutical compositions containing as active ingredient, at least one compound of general formula (I) or one of its addition salts with a pharmaceutically acceptable acid, alone or in combination with one or more inert, nontoxic excipients or vehicles.

Among the pharmaceutical compositions according to the invention, those which are suitable for oral, parenteral or nasal administration, simple or sugared tablets, sublingual tablets, sachets, packets, gelatin capsules, sublingual preparations, troches, suppositories, creams, ointments, skin gels or aerosols may be more particularly mentioned.

The dosage varies according to the age and weight of the patient, the nature and severity of the condition as well as the route of administration. The administration may be oral, nasal, rectal or parenteral. It ranges generally between 100 mg and 1 g for a treatment in one or more doses per 24 hours.

The following examples illustrate the invention and do not imply any limitation.

Preparations A to E do not enable the compounds of the invention to be obtained but lead to intermediates which are useful during synthesis of the compounds of the invention.

PREPARATION A

2-Hydroxy-4-[2-(dimethylamino)ethoxy]benzaldehyde

A mixture containing 0.8 mole of 2,4-dihydroxy-benzaldehyde, 0.8 mole of 2-chloro-1-dimethylaminoethane and 1.6 mole of potassium carbonate in 1200 ml of anhydrous methyl ethyl ketone is refluxed for 1 hour 30 minutes with stirring.

After cooling, the precipitate formed is filtered and washed with methyl ethyl ketone. The filtrate is then evaporated and leads to a brown oil which is purified by chromatography of a silica column using a dichloromethane-methanol mixture (90/10) as eluting solvent. The expected product is then obtained after recrystallization from isopropanol.

Melting point: 82-83° C.

| | Elemental microanalysis: | | |
|---|---|---|---|
| | C % | H % | N % |
| Calculated | 63.14 | 7.23 | 6.69 |
| Found | 63.24 | 7.15 | 6.58 |

PREPARATION B

2-Hydroxy-5-[2-(dimethylamino)ethoxy]benzaldehyde

The expected product is obtained in the form of a pale yellow oil using the same procedure as that described in preparation A but replacing 2,4-dihydroxy-benzaldehyde with 2,5-dihydroxy benzaldehyde.

|  | Elemental microanalysis: | | |
|---|---|---|---|
|  | C % | H % | N % |
| Calculated | 63.14 | 7.23 | 6.69 |
| Found | 62.92 | 7.17 | 6.73 |

PREPARATION C

2-Hydroxy-4-(ethoxycarbonylmethoxy)-benzaldehyde

By carrying out the procedure as in preparation A but replacing 2-chloro-1-dimethylaminoethane with ethyl bromoacetate and by refluxing the mixture for 3 hours, the expected product is obtained and purified by crystallization of the oily residue from toluene, leading to a white powder.

Melting point: 97-99° C.

|  | Elemental microanalysis: | |
|---|---|---|
|  | C % | H % |
| Calculated | 58.93 | 5.39 |
| Found | 59.19 | 5.50 |

PREPARATION D

N-(3-Formyl-4-hydroxybenzoyl)phenylalanine methyl ester 87 mmol of dicyclohexylcarbodiimide are added to a stirred suspension, cooled to 10° C, containing 80 mmol of 3-formyl-4-hydroxybenzoic acid (prepared according to H. WYMBERG, J. Am. Chem. Soc., 76, 4998, 1954) and 87 mmol of N-hydroxysuccinimide in 320 ml of chloroform. After re-equilibrating to room temperature, the mixture is kept stirring overnight. The precipitate is then filtered. The filtrate is cooled to 8° C. and treated dropwise, with stirring, with a suspension containing 160 mmol of phenylalanine methyl ester hydrochloride and 160 mmol of triethylamine in 100 ml of anhydrous dimethylformamide. The mixture is stirred for 3 hours at 20° C. and then for 5 hours at 50° C. After cooling and evaporation of the solvents, the residue is taken up in 400 ml of ethyl acetate. After washing this solution with 1N hydrochloric acid and then with water, the organic phase is dried and evaporated. The oily residue leads to the expected product by crystallization from toluene.

Melting point: 128-129° C.

|  | Elemental microanalysis: | | |
|---|---|---|---|
|  | C % | H % | N % |
| Calculated | 66.05 | 5.23 | 4.28 |
| Found | 66.21 | 5.34 | 4.76 |

PREPARATION E

N-(4-Formyl-3-hydroxybenzoyl)phenylalanine methyl ester

The expected product is obtained by carrying out the procedure as in preparation D but replacing 3-formyl-4-hydroxybenzoic acid with 4-formyl-3-hydroxybenzoic acid (prepared according to T. L. HULLAR et al., J. Med. Chem., 12, 420, 1968).

Melting point: 131-133° C.

|  | Elemental microanalysis: | | |
|---|---|---|---|
|  | C % | H % | N % |
| Calculated | 66.05 | 5.23 | 4.28 |
| Found | 66.21 | 5.34 | 4.76 |

EXAMPLE 1

[N,N'-Di-[4-(2-dimethylaminoethoxy)salicylidene]-ethylenediamine]oxovanadium (IV)

STAGE A: N,N'-Di-[4-(2-dimethylaminoethoxy)salicylidene]ethylenediamine 25 mmol of ethylenediamine are added dropwise, under a nitrogen atmosphere, to a solution containing 50 mmol of the compound obtained in preparation A in 50 ml of anhydrous ethanol. The mixture is refluxed for one hour.

After cooling and evaporation of the solvent, the expected product is obtained after recrystallization of the residue from cyclohexane.

Yield: 84%

Melting point: 92-94° C.

|  | Elemental microanalysis: | | |
|---|---|---|---|
|  | C % | H % | N % |
| Calculated | 65.14 | 7.74 | 12.66 |
| Found | 65.00 | 7.72 | 12.62 |

STAGE B: [N,N'-Di-[4-(2-dimethylaminoethoxy)salicylidene]ethylenediamine]oxovanadium (IV)

A solution containing 14 mmol of vanadyl sulfate pentahydrate in 40 ml of distilled water is added, with stirring at room temperature, to a solution containing 14 mmol of the compound obtained in Stage A in 50 ml of dichloromethane. The mixture is stirred for 30 minutes and then decanted. The aqueous phase, which is green in color, is diluted with 50 ml of distilled water and then filtered. The filtrate is treated with triethylamine until a basic pH is obtained, accompanied by precipitation. The aqueous phase and the precipitate are extracted with dichloromethane. This organic phase is then washed with water, dried and then evaporated.

The expected product is obtained by recrystallization of the solid residue from toluene.

Yield: 84%

Melting point: 190-192° C.

|  | Elemental microanalysis: | | | |
|---|---|---|---|---|
|  | C % | H % | N % | V % |
| Calculated | 56.80 | 6.36 | 11.04 | 10.04 |
| Found | 56.60 | 6.33 | 10.97 | 10.26 |

The following examples were obtained using the same procedure as that described in Example 1.

EXAMPLE 2

[N,N'-Di-[4-(2-dimethylaminoethoxy)salicylidene]-propylenediamine]oxovanadium (IV)

STAGE A: N,N'-Di-[4-(2-dimethylaminoethoxy)-salicylidene]propylenediamine

This stage is identical to stage A of Example 1 but ethylenediamine is replaced by propylenediamine.

Yield: 82%

Melting point: 63-65° C.

| | Elemental microanalysis: | | |
|---|---|---|---|
| | C % | H % | N % |
| Calculated | 65.77 | 7.95 | 12.27 |
| Found | 65.24 | 8.08 | 12.57 |

STAGE B: [N,N'-Di-[4-(2-dimethylaminoethoxy)salicylidene]propylenediamine]oxovanadium (IV)

This stage B is identical to stage B of Example 1.
Yield: 82%
Melting point: 208-211° C.

| | Elemental microanalysis: | | |
|---|---|---|---|
| | C % | H % | N % |
| Calculated | 57.58 | 6.57 | 10.74 |
| Found | 57.31 | 6.45 | 10.81 |

EXAMPLE 3

N,N'-Di-[4-(2 dimethylaminoethoxy)salicylidene]trans-1,2-cyclohexane)diamine]oxovanadium (IV)

STAGE A: N,N'-Di-[4-(2-dimethylaminoethoxy)salicylidene]-(trans-1,2-cyclohexane)diamine The expected product is obtained in the form of an oil by carrying out the procedure as in stage A of Example 1 but replacing ethylenediamine with (trans-1,2-cyclohexane)diamine.
Yield: 77%

| | Elemental microanalysis: | | |
|---|---|---|---|
| | C % | H % | N % |
| Calculated | 67.44 | 8.49 | 11.24 |
| Found | 67.33 | 8.57 | 11.05 |

STAGE B: [N,N'-Di-[4-(2-dimethylaminoethoxy)salicylidene](trans-1,2-cyclohexane)diamine]-oxovanadium (IV)

Stage B is identical to stage B of Example 1.
Yield: 80%
Melting point: 178-182° C.

| | Elemental microanalysis: | | |
|---|---|---|---|
| | C % | H % | N % |
| Calculated | 59.89 | 6.82 | 9.98 |
| Found | 59.89 | 6.72 | 9.76 |

EXAMPLE 4

[N,N'-Di-[5-(2 dimethylaminoethoxy)salicylidene]ethylenediamine]oxovanadium (IV)

STAGE A: N,N'-Di-[5-(2-dimethylaminoethoxy)salicylidene]ethylenediamine

The expected product is obtained by carrying out the procedure as in stage A of Example 1 but using as starting product the compound obtained in preparation B in place of the compound obtained in preparation A.
Yield: 72%
Melting point: 84-86° C.

| | Elemental microanalysis: | | |
|---|---|---|---|
| | C % | H % | N % |
| Calculated | 65.14 | 7.74 | 12.66 |
| Found | 64.93 | 8.15 | 12.78 |

STAGE B: [N,N'-Di-[5-(2-dimethylaminoethoxy)salicylidene]ethylenediamine]oxovanadium (IV)

Stage B is identical to stage B of Example 1.
Yield: 75%
Melting point: 180-184° C.

| | Elemental microanalysis: | | |
|---|---|---|---|
| | C % | H % | N % |
| Calculated | 56.80 | 6.36 | 11.04 |
| Found | 56.75 | 6.22 | 11.02 |

EXAMPLE 5

[N,N'-Di-(3,4,6-trimethyl-5-hydroxysalicylidene)ethylenediamine]oxovanadium (IV)

STAGE A: N,N'-Di-(3,4,6-trimethyl-5-hydroxysalicylidene)ethylenediamine

The expected product is obtained by carrying out the procedure as in stage A of Example 1 but using as starting product 3,4,6-trimethyl-2,5-hydroxybenzaldehyde obtained as described by A. MAYER et al., (Helvetica Chem. Acta, XLVI (II), 67, 650, 1963) in place of the compound described in preparation A.
Yield: 86%
Melting point: 225-229° C.

| | Elemental microanalysis: | | |
|---|---|---|---|
| | C % | H % | N % |
| Calculated | 68.73 | 7.34 | 7.29 |
| Found | 68.23 | 7.41 | 7.02 |

STAGE B: [N,N'-Di-(3,4,6-trimethyl-5-hydroxysalicylidene)ethylenediamine]oxovanadium (IV)

Stage B is identical to stage B of Example 1.
Yield: 81%
Melting point: >250° C.

| | Elemental microanalysis: | | |
|---|---|---|---|
| | C % | H % | N % |
| Calculated | 58.80 | 5.83 | 6.23 |
| Found | 58.64 | 5.48 | 6.59 |

EXAMPLE 6

[N N'-Di-[5-[(phenylalanine methyl ester)carbonyl]salicylidene]ethylenediamine]oxovanadium (IV)

STAGE A: N,N'-Di-[5-[(phenylalanine methyl ester)carbonyl]salicylidene]ethylenediamine The expected product is obtained by carrying out the procedure as in stage A of Example 1 but using as starting product the compound obtained in preparation D in place of the compound obtained in preparation A.
Yield: 70%
Melting point: 186-187° C.

| Elemental microanalysis: | | | |
|---|---|---|---|
| | C % | H % | N % |
| Calculated | 67.24 | 5.64 | 8.25 |
| Found | 66.99 | 5.69 | 8.40 |

STAGE B: [N,N'-Di-[5-[(phenylalanine methyl ester)carbonyl]salicylidene]ethylenediamine]oxovanadium (IV)

Stage B is identical to stage B of Example 1.
Yield: 64%
Melting point: 154–162° C.

| Elemental microanalysis: | | | |
|---|---|---|---|
| | C % | H % | N % |
| Calculated | 61.37 | 4.88 | 7.53 |
| Found | 61.25 | 4.80 | 7.56 |

EXAMPLE 7

[N,N'-Di-[4-[(phenylalanine methyl ester)carbonyl]salicylidene]ethylenediamine]oxovanadium (IV)

STAGE A: N,N'-Di-[4-[(phenylalanine methyl ester)carbonyl]salicylidene]ethylenediamine The expected product is obtained by carrying out the procedure as in stage A of Example 1 but using as starting product the compound obtained in preparation E in place of the compound obtained in preparation A.
Yield: 72%
Melting point: 162–166° C.

| Elemental microanalysis: | | | |
|---|---|---|---|
| | C % | H % | N % |
| Calculated | 67.24 | 5.64 | 8.25 |
| Found | 67.05 | 5.51 | 8.22 |

STAGE B: N,N'-Di-[4-[(phenylalanine methyl ester)carbonyl]salicylidene]ethylenediamine]-oxovanadium (IV)

Stage B is identical to stage B of Example 1.
Yield: 56%
Melting point: 252–256° C.

| Elemental microanalysis: | | | |
|---|---|---|---|
| | C % | H % | N % |
| Calculated | 61.37 | 4.88 | 7.53 |
| Found | 60.52 | 4.81 | 7.59 |

EXAMPLE 8

N,N'-(Bis-pyridoxal)ethylenediimine]oxovanadium (IV)

STAGE A: N,N'-(Bis-pyridoxal)ethylenediimine

The expected product is obtained as described in Patent EP-292761.

STAGE B: [N,N'-(Bis-pyridoxal)ethylenediimine]-oxovanadium (IV)

Stage B is identical to stage 8 of Example 1.
Yield: 82%
Melting point: >250° C.

| Elemental microanalysis: | | | |
|---|---|---|---|
| | C % | H % | N % |
| Calculated | 51.07 | 4.76 | 13.23 |
| Found | 50.77 | 4.87 | 13.23 |

EXAMPLE 9

[N,N'-Di-[4-(carboxymethyloxy)salicylidene]ethylenediamine]oxovanadium (IV), di-tertbutylamine salt STAGE A: N,N'-Di-[4-(ethoxycarbonylmethyloxy)-salicylidene]ethylenediamine The expected product is obtained by carrying out the procedure as in stage A of Example 1 but using as starting product the compound obtained in preparation C in place of the compound obtained in preparation A.
Yield: 80%
Melting point: 104–106° C.

| Elemental microanalysis: | | | |
|---|---|---|---|
| | C % | H % | N % |
| Calculated | 61.01 | 5.97 | 5.93 |
| Found | 60.87 | 6.05 | 5.85 |

STAGE B: [N,N'-Di-[4-(carboxymethyloxy)-salicylidene]ethylenediamine]oxovanadium (IV), di-tert-butylamine salt 20 ml of 1N NaOH are added, at room temperature, to a suspension containing 16 mmol of the product obtained in stage A in 100 ml of a tetrahydrofuran/water mixture (50/50). After stirring for 4 hours, the tetrahydrofuran is evaporated; the residual aqueous phase is washed with dichloromethane and treated with a solution containing 10 mmol of vanadyl sulfate pentahydrate in 20 ml of distilled water. The reaction mixture is kept stirring at room temperature for omol of vanadyltes and then acidified with 3N hydrochloric acid until a pH value of 3–4 is obtained. The precipitate formed is filtered, washed with water until neutral and dried.

The corresponding tert-butylamine salt is formed by stirring the precipitate formed in an aqueous solution of tert-butylamine and purified by recrystallization from a water/acetone mixture (30/70).
Yield: 53%
Melting point: 235–240° C.

| Elemental microanalysis: | | | |
|---|---|---|---|
| | C % | H % | N % |
| Calculated | 53.59 | 6.42 | 8.93 |
| Found | 53.55 | 6.17 | 8.28 |

EXAMPLE 10

N,N'-Bis[(5-pyridoxal phosphate)ethylenediimine]oxovanadium (IV), tetrasodium salt STAGE A: N,N'-(bis-pyridoxal phosphate)ethylenediimine, tetrasodium salt The expected product is obtained as described in Patent EP 290047.

STAGE B: N,N'-Bis[(5-pyridoxal phosphate)ethylenediimine]oxovanadium (IV), tetrasodium salt A solution containing 10 mmol of the product obtained in stage A in 20 ml of distilled water is treated at room temperature, with stirring, with a solution containing 10 mmol of vanadyl sulfate penta-hydrate in 15 ml of distilled water.

After stirring for one hour, the precipitate formed is filtered, dried and then taken up in 100 ml of water. The suspension is treated with 12 ml of 1N NaOH. The solution is filtered and evaporated. The expected product is obtained by recrystallization of the residue from a water/ethanol mixture (30/70).

Yield: 76%

Melting point: >250° C.

| | Elemental microanalysis: | | |
|---|---|---|---|
| | C % | H % | N % |
| Calculated | 32.21 | 2.70 | 8.35 |
| Found | 32.55 | 3.79 | 7.85 |

PHARMACOLOGICAL STUDIES OF THE COMPOUNDS OF THE INVENTION

EXAMPLE 11

Insulin-like effects in vitro

Insulin-like effects of the compounds of the invention were studied in vitro on adipose tissue fragments by measuring the metabolism of carbon 14-labelled glucose and the capture of 2-deoxyglucose according to the techniques described by M. RODBELL (J. Biol. Chem., 239, 375, 1964) and by J. M. OLEFSKY (J. Clin. Invest., 56, 1499, 1975)

The results obtained with the compounds of the invention were compared with the response to insulin which represents +100% at $10^{-9}$M. The reference product used is sodium orthovanadate. The results obtained at $10^{-4}$M are collated in the table below:

| Ex | Metabolism of labelled glucose | Capture of 2-deoxyglucose |
|---|---|---|
| Ex 1 | +43% | +78% |
| Ex 3 | +51% | +96% |
| Ex 4 | +56% | +113% |
| Sodium orthovanadate | +23% | +95% |

These results show that the metabolism of labelled glucose and the capture of 2-deoxyglucose by the adipose tissue are increased by the presence of insulin (+100%) or the compounds mentioned.

EXAMPLE 12

Hypoglycemic response in vivo

The hypoglycemic response was studied after oral administration of the compounds of the invention, after suspension in a 20% solution of Senegal gum, to rats rendered diabetic by the injection of streptozotocin (65 mg/kg) according to the technique described by A. JUNOD et al., (J.Clin. Invest., 48, 11, 2129, 1969).

The results, indicating the decrease in glycemia observed after 10 days of treatment with the compounds of the invention at a dose of 2 12.5 mg/kg/day, are collated in the table below. The reference product used is sodium orthovanadate.

| Compound | Decrease in glycemia (%) | Amount of corresponding vanadium (mg/kg) |
|---|---|---|
| Ex 1 | −45 | 2,50 |
| Ex 5 | −31 | 2,83 |
| Ex 7 | −41 | 1,71 |
| Sodium orthovanadate | −48 | 6,93 |

These results show that the decrease in glycemia observed with the abovementioned compounds is between −31% and −45% for amounts of vanadium 2.5 to 4 times lower than the amount of vanadium corresponding to the administration, under the same conditions, of sodium orthovanadate which causes a decrease in glycemia of −48%.

PHARMACEUTICAL COMPOSITION

EXAMPLE 13

Tablet: preparation formula for 1000 tablets containing a dose of 100 mg

| Compound of Example 1 | 100 g |
|---|---|
| Hydroxypropyl cellulose | 2 g |
| Wheat starch | 10 g |
| Lactose | 100 g |
| Magnesium stearate | 3 g |
| Talc | 3 g |

We claim:

1. A compound of formula (I):

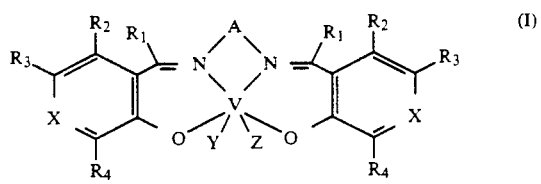

in which:

$R_1$ and $R_4$, which are identical or different, represent hydrogen or linear or branched ($C_1$-$C_6$) alkyl, $R_2$ represents hydrogen, linear or branched ($C_1$-$C_6$) alkyl, hydroxymethyl, —$CH_2OPO(OH)_2$, or —$CH_2OPO(ONa)_2$, $R_3$ represents hydroxyl, or any one of the following groups:

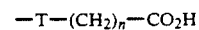

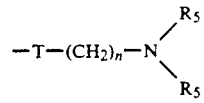

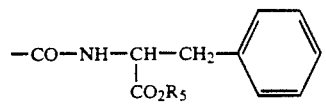

in which:

T represents oxygen or sulfur, n represents an integer of 1 to 4, inclusive $R_5$ represents hydrogen or linear or branched ($C_1$-$C_6$) alkyl, X represents CH or C-($C_1$-$C_6$)alkyl A represents alkylene of formula —(CH₂)p— in which p represents an integer of 2 to 4, inclusive, optionally substituted by one or more linear or branched (C₁-C₄) alkyl, or any one of the following radicals:

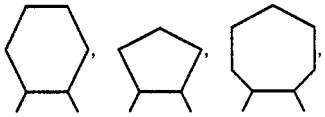

Y and Z together form oxygen or, alternatively, Y and Z simultaneously represent two hydroxyl groups, and its isomers, as well as its addition salts with a pharmaceutically-acceptable acid or base.

2. A compound of formula (I):

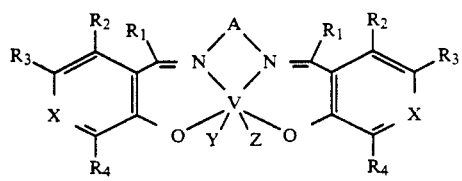

in which:
R₁ and R₄, which are identical or different, represent hydrogen or linear or branched (C₁-C₆) alkyl,
R₂ represents hydrogen, linear or branched (C₁-C₆) alkyl, hydroxymethyl, —CH₂OPO(OH)₂, or —CH₂OPO(ONa)₂,
R₃ represents hydrogen, linear or branched (C₁-C₆) alkyl, hydroxyl, or any one of the following groups:

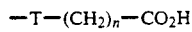

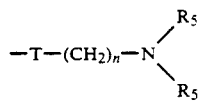

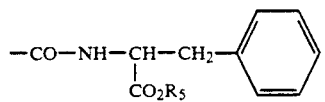

in which:
T represents oxygen or sulfur,
n represents an integer of 1 to 4, inclusive,
R₅ represents hydrogen or linear or branched (C₁-C₆) alkyl
X represents

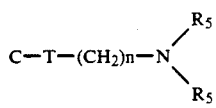

as above defined, or

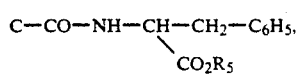

-continued or

C—O—CH₂—CO₂H,

A represents alkylene of formula —(CH₂)p— in which p represents an integer of 2 to 4, inclusive, optionally substituted by one or more linear or branched (C₁-C₄) alkyl, or any one of the following radicals:

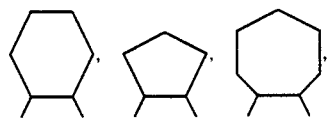

Y and Z together form oxygen or, alternatively, simultaneously represent two hydroxyl groups, its isomers, as well as its addition salts with a pharmaceutically-acceptable acid or base.

3. A compound of formula (I):

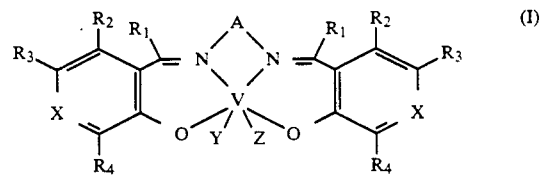

in which:
R₁ and R₄, which are identical or different, represent hydrogen or linear or branched (C₁-C₆) alkyl,
R₂ represents hydrogen, linear or branched (C₁-C₆) alkyl, hydroxymethyl, —CH₂OPO(OH)₂ or —CH₂OPO(ONa)₂,
R₃ represents hydrogen, linear or branched (C₁-C₆) alkyl, hydroxyl, or any one of the following groups:

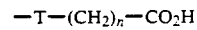

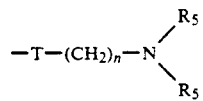

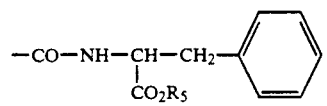

in which:
T represents oxygen or sulfur,
n represents an integer of 1 to 4, inclusive,
R₅ represents hydrogen or linear or branched (C₁-C₆) alkyl,
X represents (CH₃)₂N—CH₂—CH₂—O—C,
A represents alkylene of formula —(CH₂)p— in which p represents an integer of 2 to 4, inclusive, optionally substituted by one or more linear or branched (C₁-C₄) alkyl, or any one of the following radicals:

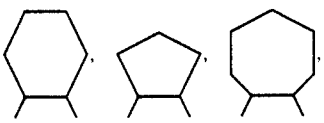

Y and Z together form oxygen or, alternatively, simultaneously represent two hydroxyl groups,
and its isomers, as well as its addition salts with a pharmaceutically-acceptable acid or base.

4. A compound as claimed in claim 1, wherein A represents ethylene, its enantiomers, as well as its addition salts with a pharmaceutically-acceptable acid or base.

5. A compound as claimed in claim 1, wherein Y and Z together form oxygen, its enantiomers, as well as its addition salts with a pharmaceutically-acceptable acid or base.

6. The compound [N,N'-di-[4-(2-dimethylaminoethoxy) salicylidene] ethylenediamine] oxovanadium (IV), as well as its addition salts with a pharmaceutically-acceptable acid.

7. A method for treating an animal or human living body afflicted with diabetes or obesity comprising the step of administering to the living body an amount of a compound of formula (I):

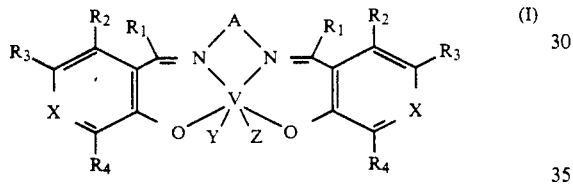

in which:
$R_1$ and $R_4$, which are identical or different, represent hydrogen or linear or branched ($C_1$-$C_6$) alkyl,
$R_2$ represents hydrogen, linear or branched ($C_1$-$C_6$) alkyl, hydroxymethyl, $-CH_2OPO(OH)_2$, or $-CH_2OPO(ONa)_2$,
$R_3$ represents hydrogen, linear or branched ($C_1$-$C_6$) alkyl, hydroxyl, or any one of the following groups:

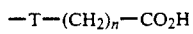

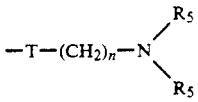

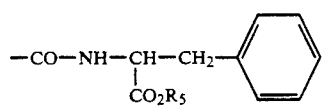

in which:
T represents oxygen or sulfur,
n represents an integer of 1 to 4, inclusive,
$R_5$ represents hydrogen or linear or branched ($C_1$-$C_6$) alkyl,
X represents CH or CR'$_3$ (in which R'$_3$ has the same meaning as $R_3$ except in the case where $R_3$ represents hydroxyl),
A represents alkylene of formula $-(CH_2)p-$ in which p represents an integer of 2 to 4, inclusive, optionally substituted by one or more linear or branched ($C_1$-$C_4$) alkyl, or any one of the following radicals:

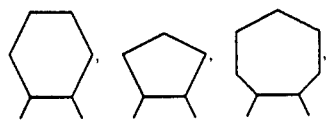

Y and Z together form oxygen, or alternatively, simultaneously represent two hydroxyl groups, provided that:
a when:
A represents ethylene (optionally substituted by alkyl), and
$R_2$, $R_3$ and $R_4$ simultaneously represent hydrogen and $R_1$ represents hydrogen or alkyl,
then X does not represent CH,
b when:
A represents a group

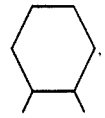

and
$R_1$, $R_2$ and $R_3$ simultaneously represent hydrogen, and $R_4$ represents hydrogen or alkyl,
then X does not represent CH,
and its isomers, as well as its addition salts with a pharmaceutically-acceptable acid or base, which is effective for alleviation of said condition.

8. A pharmaceutical composition useful for treating diabetes or obesity comprising as active principle an effective amount of a compound of formula (I):

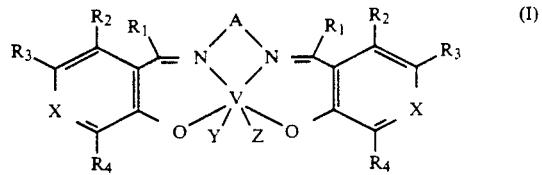

in which:
$R_1$ and $R_4$, which are identical or different, represent hydrogen or linear or branched ($C_1$-$C_6$) alkyl,
$R_2$ represents hydrogen, linear or branched ($C_1$-$C_6$) alkyl, hydroxymethyl, $-CH_2OPO(OH)_2$, or $-CH_2OPO(ONa)_2$,
$R_3$ represents hydrogen, linear or branched ($C_1$-$C_6$) alkyl, hydroxyl, or any one of the following groups:

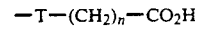

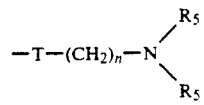

-continued

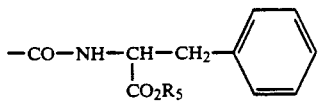

in which:

T represents oxygen or sulfur, n represents an integer of 1 to 4, inclusive, $R_5$ represents hydrogen or linear or branched ($C_1$-$C_6$) alkyl, X represents CH or $CR'_3$ (in which $R'_3$ has the same meaning as $R_3$ except in the case where $R_3$ represents hydroxyl), A represents alkylene of formula —$(CH_2)p$— in which p represents an integer of 2 to 4, inclusive, optionally substituted by one or more linear or branched ($C_1$-$C_4$) alkyl, or any one of the following radicals:

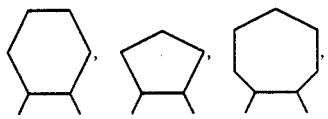

Y and Z together form oxygen, or, alternatively, simultaneously represent two hydroxyl groups, provided that:

a when:

A represents ethylene (optionally substituted by alkyl), and $R_2$, $R_3$ and $R_4$ simultaneously represent hydrogen and $R_1$ represents hydrogen or alkyl, then X does not represent CH, b when:

A represents a group

and $R_1$, $R_2$ and $R_3$ simultaneously represent hydrogen, and $R_4$ represents hydrogen or alkyl, then X does not represent CH, and its isomers, as well as its addition salts with a pharmaceutically acceptable acid or base together with one or more pharmaceutically-acceptable excipients or vehicles.

9. A method for treating of an animal or human living body afflicted with diabetes or obesity comprising the step of administering to the living body an amount of [N,N'-di-[4-(2-dimethylaminoethoxy)salicylidene]ethylenediamine]-oxovanadium (IV) or a pharmaceutically-acceptable acid addition salt thereof which is effective for alleviation of said condition.

10. A pharmaceutical composition useful for treating diabetes or obesity comprising as active principle an effective amount of [N,N'di-[4-(2-dimethylaminoethoxy)salicylidene]ethylenediamine]-oxovanadium (VI) or a pharmaceutically-acceptable acid addition salt thereof, together with one or more pharmaceutically-acceptable excipients or vehicles.

* * * * *

UNITED STATES PATENT AND TRADEMARK OFFICE
CERTIFICATE OF CORRECTION

PATENT NO. : 5,266,565

DATED : November 30, 1993

INVENTOR(S) : Jean-Michel Lacoste, Jaques Duhault, Denis Ravel

It is certified that error appears in the above-indentified patent and that said Letters Patent is hereby corrected as shown below:

Title Page, [57], Col. 2, line 3; correct the spelling of "hydrogen".
Col. 4, line 3;  insert a period at the end of the line.
Col. 7, line 23; insert -- [ -- before "N,N".
Col. 7, line 24; insert -- -( -- before "trans".
Col. 7, line 56; insert a hyphen at the end of the line after "(2".
Col. 8, line 23; delete "e" at the end of the line.
Col. 8, line 24; correct the spelling of "ethylenediamine".
Col. 9, line 58; insert -- [ -- at the beginning of the line.
Col. 9, line 66; change "8" to -- B --.
Col. 10, line 10; delete "e" at the end of the line.
Col. 10, line 11; correct the spelling of "ethylenediamine".
Col. 10, line 40; delete "for omol of vanadyl".
Col. 10, line 41; delete "tes" at the beginning of the line.
Col. 10, line 63; delete "e" at the end of the line.
Col. 10, line 64; correct the spelling of "ethylenediimine".
Col. 11, line 30; "carbon 14" should read -- carbon$^{14}$ --.
Col. 11, line 35; insert a period at the end of the line.
Col. 11, line 66; "2 12.5" should read -- 2 x 12.5 --.

UNITED STATES PATENT AND TRADEMARK OFFICE
CERTIFICATE OF CORRECTION

PATENT NO. : 5,266,565
DATED : November 30, 1993
INVENTOR(S) : Jean-Michel Lacoste, Jaques Duhault, Denis Ravel It is certified that error appears in the above-indentified patent and that said Letters Patent is hereby corrected as shown below:

```
Col. 12, lines 5-10;  all commas should be replaced by periods.
Col. 14, line 39;     "CH-" last instance should read -- CH₂- --.
Col. 15, line 40;     delete the subscript "2" first instance.
Col. 16, line 14;     "a" should be underlined.
Col. 16, line 20;     "then" should be underlined.
Col. 16, line 21;     "b" should be underlined.
Col. 16, line 34;     "then" should be underlined.
Col. 17, line 33;     "a" should be underlined.
Col. 18, line 3;      "then" should be underlined.
Col. 18, line 4;      "b" should be underlined.
Col. 18, line 16;     "then" should be underlined.
```

Signed and Sealed this

Twelfth Day of July, 1994

Attest:

BRUCE LEHMAN

*Attesting Officer*      *Commissioner of Patents and Trademarks*